(12) United States Patent
Porro

(10) Patent No.: US 7,074,958 B2
(45) Date of Patent: Jul. 11, 2006

(54) INTEGRATED PROCESS FOR UREA/MELAMINE PRODUCTION AND RELATED PLANT

(75) Inventor: Lino Porro, Novedrate (IT)

(73) Assignee: Urea Casale S.A. (CH)

( * ) Notice: Subject to any disclaimer, the term of this patent is extended or adjusted under 35 U.S.C. 154(b) by 0 days.

(21) Appl. No.: 11/179,691

(22) Filed: Jul. 11, 2005

(65) Prior Publication Data

US 2006/0052637 A1  Mar. 9, 2006

(30) Foreign Application Priority Data

Sep. 9, 2004  (EP) .................. 04021455

(51) Int. Cl.
C07C 273/12 (2006.01)
B05L 10/00 (2006.01)
C07D 251/60 (2006.01)

(52) U.S. Cl. .................. 564/67; 422/187; 422/188; 422/189; 569/70; 569/71; 569/72; 544/201

(58) Field of Classification Search ................ 544/201; 422/187, 188, 189; 564/67, 70, 71, 72
See application file for complete search history.

(56) References Cited

U.S. PATENT DOCUMENTS

| 3,239,522 A | 3/1966 | Cook et al. |
| 3,723,430 A | 3/1973 | Kokubo et al. |
| 6,586,629 B1 * | 7/2003 | Coufal .................. 564/67 |

FOREIGN PATENT DOCUMENTS

GB  1 216 100 A  12/1970

* cited by examiner

Primary Examiner—Peter O'Sullivan
(74) Attorney, Agent, or Firm—Akerman Senterfitt

(57) ABSTRACT

An integrated process for urea/melamine production. In the process, urea is synthesized from ammonia and carbon dioxide, obtaining molten urea and a gaseous mixture comprising steam and ammonia. The gaseous mixture is condensed, obtaining a cold aqueous ammoniacal solution. Melamine is synthesized from urea with formation of off-gases, comprising ammonia and carbon dioxide. The off-gases are absorbed in at least one fraction of the cold aqueous ammonical solution, with formation of a carbamate aqueous solution. The carbamate aqueous solution is decomposed, obtaining ammonia, carbon dioxide and steam, and a residual aqueous ammoniacal solution. The ammonia and the carbon dioxide are recycled for the urea synthesis. The residual aqueous ammoniacal solution obtained is treated to recover ammonia and carbon dioxide for the urea synthesis.

12 Claims, 3 Drawing Sheets

INTEGRATED PROCESS FOR UREA/MELAMINE PRODUCTION AND RELATED PLANT

FIELD OF APPLICATION

The present invention refers, in its most general aspect, to melamine production from urea.

In particular this invention concerns a process of the so-called integrated type for urea/melamine production comprising a first urea synthesis operating step, from carbon dioxide and ammonia, and a second step in which at least a part of the urea thus produced is used for the melamine synthesis.

More specifically the present invention refers to an integrated process of the above type in which the off-gases from the melamine synthesis step are treated for a recovery of carbon dioxide and ammonia, comprised in them, that are recycled at the urea synthesis step.

In the rest of the description, the gas mixture comprising carbon dioxide and ammonia, for the sake of brevity, is sometimes called urea synthesis gas.

The present description also refers to a plant for urea/melamine production according to the aforementioned integrated process.

PRIOR ART

It is known that, in the field of the melamine production from urea, for some time the use of a so-called integrated process has become established, according to which the urea necessary for the aforementioned production is obtained from ammonia and carbon dioxide in a step that is preliminary to the melamine synthesis.

And it is known that for an improved integration of such a process, an appropriate treatment of the off-gases, freed by the melamine synthesis reaction, is generally provided to recover ammonia and carbon dioxide from them, to be recycled to the urea synthesis.

For such a purpose, in accordance with the prior art, the off-gases are absorbed in an aqueous ammoniacal solution, suitably cooled, obtaining an carbamate aqueous solution; then this carbamate aqueous solution is decomposed, obtaining carbon dioxide and ammonia, which are recycled to the urea production, and a residual aqueous ammoniacal solution.

Generally the residual aqueous ammoniacal solution is recycled, after possible cooling, to the absorption step of the off-gases.

This technique of urea synthesis gas recovery from the off-gases of the melamine synthesis step, whilst being effective and even advantageous from some points of view, has recognised drawbacks.

Amongst these, a main drawback is linked to the fact that such a technique requires specific equipment and devices to carry it out, intended for that sole purpose and sized to carry out the treatment of the off-gases described above, involving a large increase in costs for the materials and the apparatuses used, as well as for their management.

Indeed, it should be noted, for example, that to ensure the absorption of the off-gases, it is necessary to cool the residual aqueous ammoniacal solution before it is entered into the absorption column, so requiring the use of an appropriate refrigerator.

SUMMARY OF THE INVENTION

The problem underlying the present invention is that of providing an integrated process for urea/melamine production of the type mentioned above, which allows a reduced amount of equipment to be used for the treatment of the off-gases, above all without necessarily requiring the use of specific and suitably sized equipment.

This problem is solved, according to the present invention, by an integrated process for urea/melamine production comprising the operating steps of:

(a)—urea synthesis from ammonia and carbon dioxide, obtaining molten urea and a gaseous mixture comprising steam and ammonia;

(b)—condensation of said gaseous mixture comprising steam and ammonia, obtaining a cold aqueous ammoniacal solution;

(c)—melamine synthesis from urea with formation of off-gases, comprising ammonia and carbon dioxide;

said process being characterised in that it comprises the further steps of:

(d)—absorption of said off-gases in at least one fraction of the cold aqueous ammoniacal solution obtained in said step (b), with formation of a carbamate aqueous solution;

(e)—decomposition of said carbamate aqueous solution, obtaining ammonia, carbon dioxide and steam, and a residual aqueous ammoniacal solution;

(f)—recycling of the ammonia and of the carbon dioxide obtained in said step (e) for the urea synthesis;

(g)—treatment of the residual aqueous ammoniacal solution obtained in said step (e) for the recovery of ammonia and carbon dioxide for the urea synthesis.

Preferably the residual aqueous ammoniacal solution obtained in step (e) is added to part of the cold aqueous ammoniacal solution obtained in step (b), and not used for the absorption of the off-gases, to constitute a single aqueous ammoniacal solution to be subjected to urea synthesis gas recovery treatment.

Further characteristics and the advantages of the invention shall become clearer from the following description of an embodiment thereof, made for indicating and not limiting purposes, with reference to the attached figures.

DETAILED DESCRIPTION OF A PREFERRED EMBODIMENT

Figure 1:
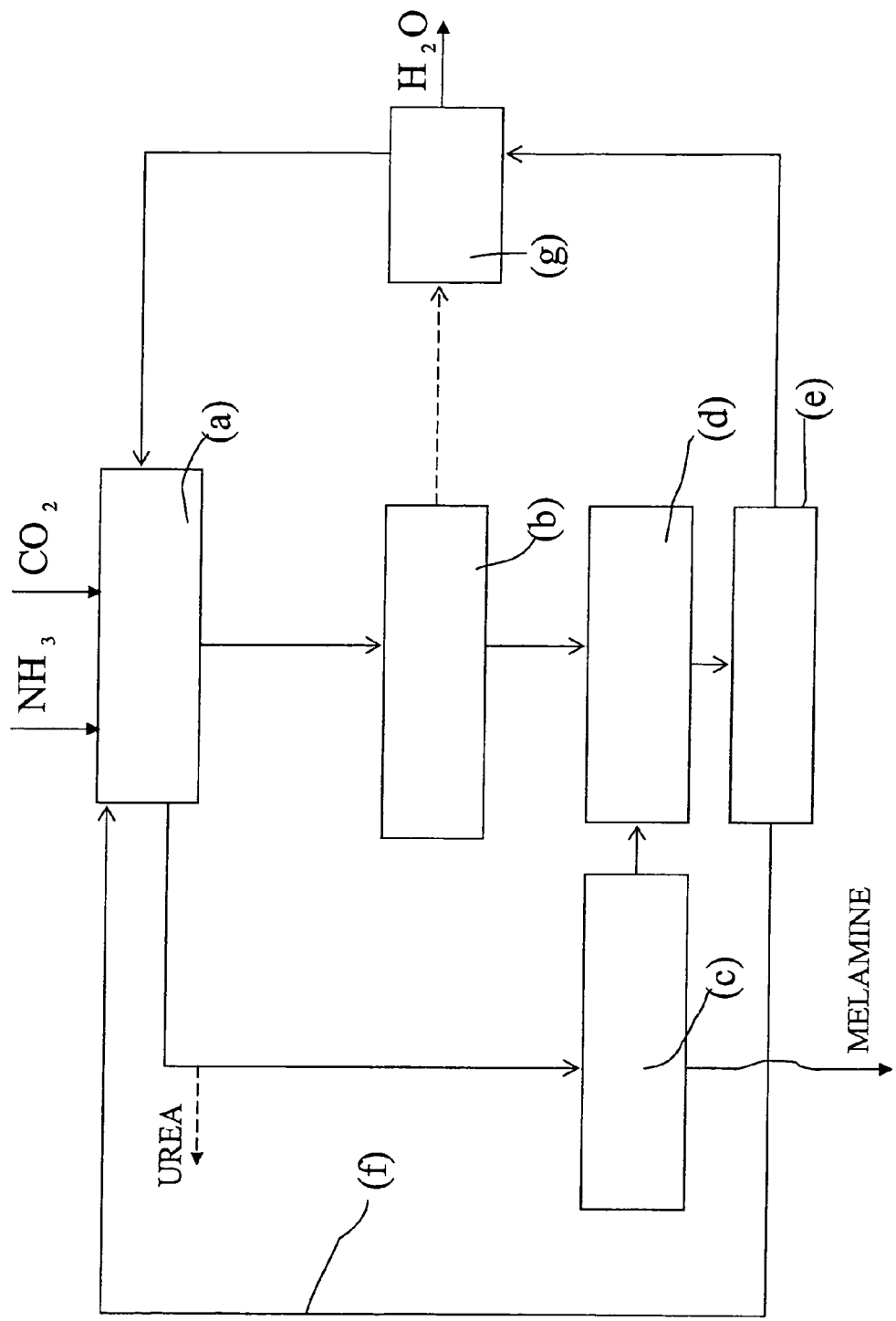
FIG. 1 illustrates a block diagram relative to the integrated process for urea/melamine production, according to the present invention.

With reference to FIG. 1, the integrated process for urea/melamine production, according to the invention, comprises a first step (a) in which urea is synthesised from ammonia and carbon dioxide, obtaining molten urea and a gaseous mixture comprising steam and ammonia.

Preferably the urea synthesis is carried out according to a so-called total recycling technology and more preferably with a so-called stripping technology. The urea is initially synthesised at high pressure, and then the urea in aqueous solution thus obtained is separated from the unreacted synthesis components in a urea recovery step through one or more stages of decomposition and condensation at consecutively decreasing pressures. Preferably a medium pressure decomposition and condensation stage, conducted at about 15–30 bar, and a low pressure decomposition and condensation stage, conducted at about 2–10 bar, are provided.

More specifically in the first step (a), ammonia and carbon dioxide are made to react in urea in aqueous solution, which is treated in a known way in said urea recovery step and in at least one evaporation step, to separate on the one hand molten urea and on the other hand a gaseous mixture comprising steam and ammonia, which mainly comprises water, ammonia, carbon dioxide.

In a subsequent step (b), the aforementioned gaseous mixture comprising steam and ammonia is condensed to obtain a cold aqueous ammoniacal solution.

Preferably, the condensation is carried out in a vacuum manner.

The process also comprises a treatment step of the waste water (g) which is predisposed to treat—according to the invention—a possible part of the cold aqueous ammoniacal solution to recover ammonia and carbon dioxide from it for the urea synthesis.

It should be noted that steps (a), (b) and (g) described up to now are, per se, steps that are generally known in a urea production process.

The integrated process according to the invention comprises an operating step (c) of melamine synthesis.

In this specific case, the melamine synthesis takes place by making to react at least part of the molten urea, produced in the operating step (a), through low pressure catalysis, preferably between 0.1 and 10 bar. The low pressure catalytic synthesis provides, in a known way, the obtaining of a gaseous mixture having a high temperature, for example about 400° C., and comprising melamine, carbon dioxide, ammonia, unreacted urea, and further inert by-products. The gaseous mixture is preferably cooled, filtered and crystallised to obtain, on the one hand, melamine crystals and, on the other hand, a flow of off-gases, containing carbon dioxide and ammonia.

In the specific case of low pressure catalytic synthesis of melamine, the pressure value of the off-gases produced is between 0.1 and 8 bar, preferably it is equal to about 1.1 bar.

In an operating step (d) the off-gases thus produced are made to absorb in aqueous solution, i.e. they are condensed, to obtain a carbamate aqueous solution.

According to the invention, the off-gases are absorbed in at least a fraction of the aforementioned cold aqueous ammoniacal solution, obtained during the condensation operating step (b).

In this way, according to the invention, the cold aqueous ammoniacal solution itself is exploited to condense the off-gases.

Preferably the condensation is carried out in a plurality of successive stages.

In a first stage, the off-gases are mixed with the cold aqueous ammoniacal solution obtaining a biphasic mixture comprising an aqueous solution of carbamate and ammonia, carbon dioxide and water in steam phase.

In a second stage, the steams present in the biphasic mixture are condensed in the form of carbamate aqueous solution through indirect heat exchange with a cooling means.

In a third stage, to ensure the completion of the condensation, after the indirect heat exchange, the gases (steams) possibly present in the carbamate aqueous solution are separated from it and are condensed through washing with water in a separation column, so as to be able to be recovered. The recovered gases are preferably recycled and condensed further through the indirect heat exchange of the aforementioned second stage of condensation, whereas possible gaseous by-products, that cannot be condensed and that are inert, are eliminated.

Preferably the condensation stages described above are conducted at the same effective pressure of the off-gases.

In a subsequent stage (e), the carbamate aqueous solution is decomposed to obtain, on the one hand, a gaseous mixture comprising urea synthesis gases, such as carbon dioxide and ammonia, and steam, on the other hand, a residual aqueous ammoniacal solution.

Preferably the carbamate aqueous solution, before being decomposed, is heated.

In a preferred solution, the decomposition of the carbamate is obtained through indirect heat exchange with steam at a temperature of 165° C.–170° C. and at a pressure of about 18–20 bar.

In these conditions, the gaseous mixture that is obtained from the decomposition of carbamate comprises, in addition to carbon dioxide and ammonia, also steam. Such a mixture is suitable for being treated in the urea recovery step and in particular in the medium pressure stage.

According to another characteristic, the integrated process according to the invention comprises a further step during which the residual ammoniacal solution obtained from the decomposition of the carbamate aqueous solution is treated to recover ammonia and carbon dioxide from it, possibly not separated during the decomposition step. This allows a complete recovery of carbon dioxide and ammonia to be obtained as synthesis gas for the urea synthesis.

Preferably, the residual aqueous ammoniacal solution is decomposed directly in the waste water treatment step (g) described above, which, as already mentioned, is provided to recover the urea synthesis gases.

In this way, in the waste water treatment step (g) both part of the cold aqueous ammoniacal solution, possibly not used for the absorption of the off-gases, and the residual aqueous ammoniacal solution are treated.

It can easily be observed from the description made up to now that the integrated process for urea/melamine production according to the present invention provides a greater integration, with respect to the prior art, between the steps commonly known for the synthesis and the treatment of urea, (a), (b), (g) mentioned above, and the operating steps of treatment of the off-gases (d) and (e) produced by the melamine synthesis.

This greater integration allows a series of advantages.

A first advantage lies in the fact that the cold aqueous ammoniacal solution itself produced during the condensation step is used to absorb the off-gases. The cold aqueous ammoniacal solution is also advantageously diluted in a suitable manner, as well as cooled to the right temperature, to obtain the desired condensation of the off-gases.

Another advantage can be identified in the fact that the residual aqueous ammoniacal solution obtained during the decomposition step of the carbamate aqueous solution is treated so as to be able to recycle possible urea synthesis gases (ammonia and carbon dioxide) that have not been separated.

Moreover, the treatment of the residual aqueous ammoniacal solution is advantageously carried out without additional costs in the same step of waste water treatment, which, as hinted above, is generally provided in a urea synthesis process.

A further advantage lies in the fact that the recovery of the urea synthesis gases in the treatment step of the waste water, avoids the need for a high desorption process of the urea synthesis gases during the decomposition step of the carbamate aqueous solution, so that reduced size equipment can be used, both for the desorption of the urea synthesis gases and consequently also for the absorption of the off-gases.

A further advantage of the greater integration lies in the fact that it is possible to vary the fractions of cold aqueous ammoniacal solution to be used in the absorption step of the off-gases and in the treatment step of the waste water according to determined process modality.

Yet another advantage of the present process is given by the fact that the vapours comprising ammonia and carbon dioxide obtained from the treatment of the off-gases according to the invention and recycled to the urea synthesis step are low in water to the great advantage of the urea conversion yield.

Figure 2:
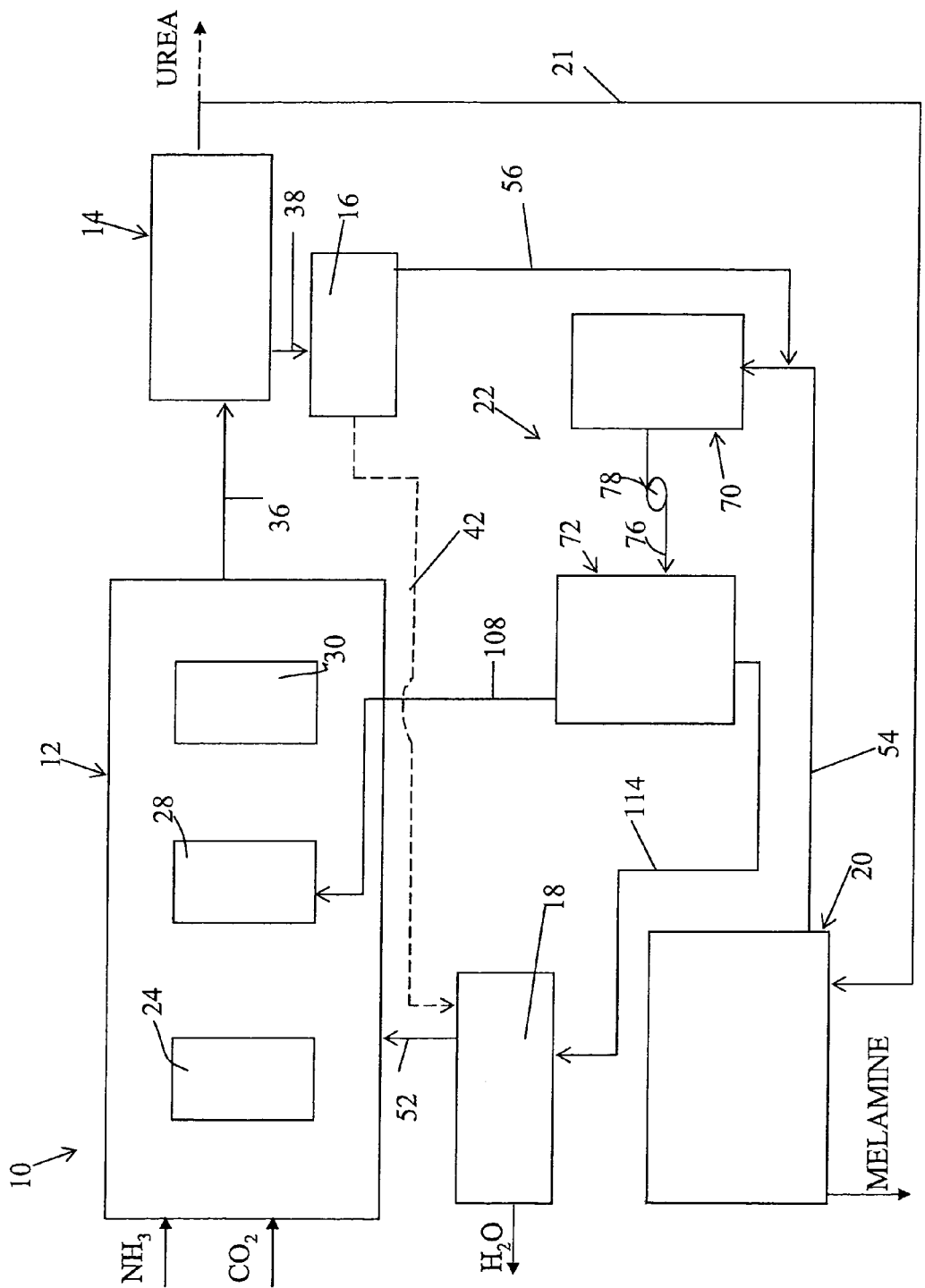
FIG. 2 schematically illustrates an integrated plant, for carrying out the process according to the present invention.
Figure 3:
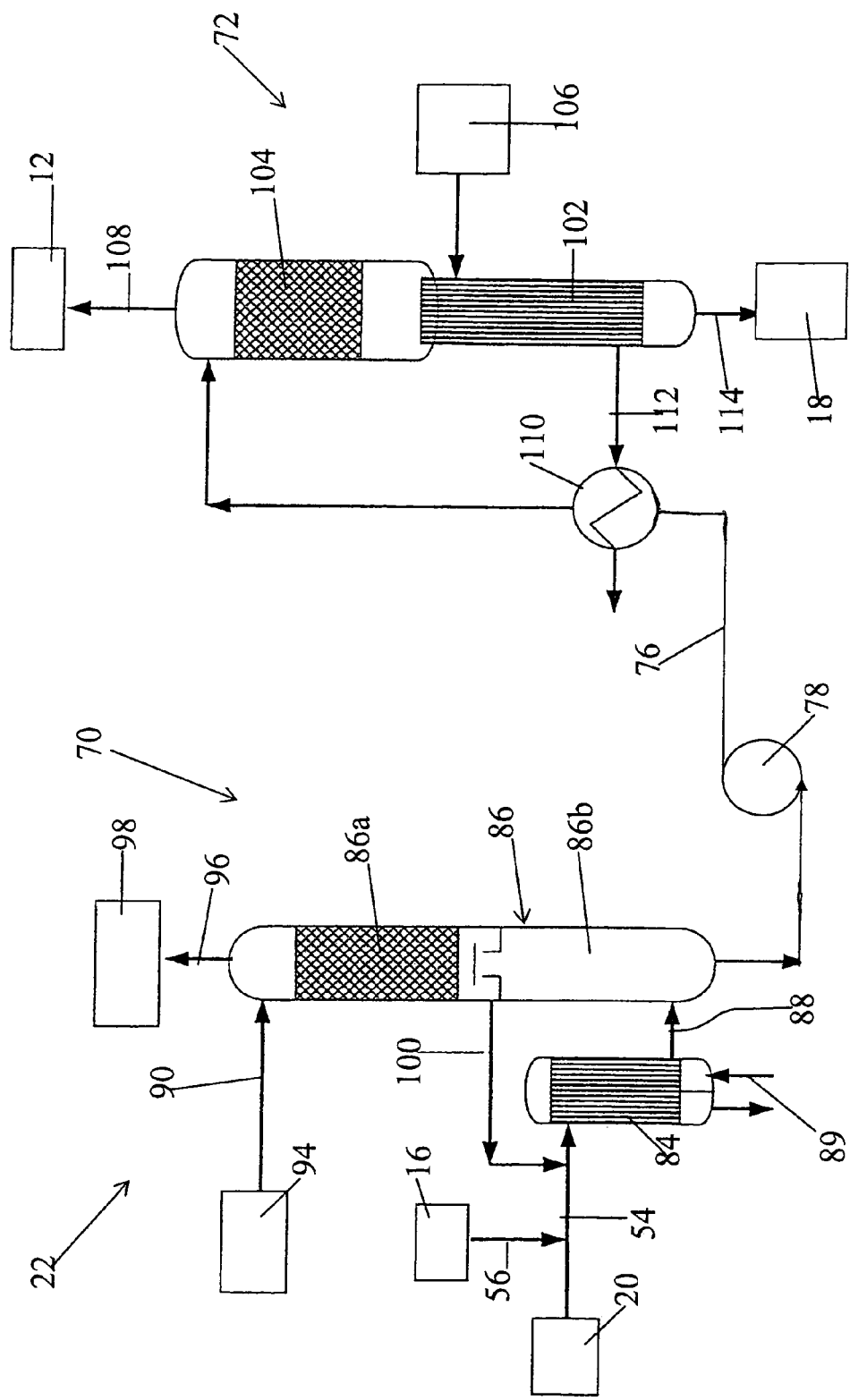
FIG. 3 schematically illustrates a detail of the plant of FIG. 2.

With reference to FIGS. 2 and 3, an integrated plant 10 for urea/melamine production according to the process described above, also object of the present invention, shall now be illustrated.

In such figures, for the sake of brevity and clarity, only those parts of the plant necessary for the description of the present invention are schematically indicated. Moreover, with the term "connection line" we mean to indicate a structural connection such as a duct or a piping that is per se known.

In particular, the integrated plant 10 comprises a urea synthesis and recovery section 12 for obtaining urea in aqueous solution.

The urea synthesis and recovery section 12 is, in the example of FIG. 2, of the total recycle type, and comprises an actual urea synthesis reactor 24, preferably operating at a high pressure, between about 130 and 300 bar, a medium pressure recovery stage 28, operating at about 15–30 bar, and a low pressure recovery stage 30, operating at a pressure of about 2–10 bar.

In the rest of the description, for the sake of brevity of presentation, with the term urea synthesis and recovery section 12 we therefore mean the assembly of the reactor 24 and of the stages 28 and 30 mentioned above.

The plant 10 also comprises a urea treatment section 14, which is in fluid communication with the synthesis and recovery section 12 through a connection line 36, and predisposed to obtain molten urea and a gaseous mixture comprising steam and ammonia from the urea in aqueous solution.

In particular, the urea treatment section 14 preferably comprises an evaporation unit in which the urea is separated in molten state from the gaseous mixture comprising steam, ammonia and carbon dioxide.

The plant 10 also comprises a condensation section 16, which is in fluid communication with the section 14 through a connection line 38.

The condensation section 16 substantially comprises a condenser, preferably operating in a vacuum (preferably, the section 14 also operates in a vacuum), and predisposed for the condensation of the gaseous mixture comprising steam and ammonia.

In the section 16 a cold aqueous ammoniacal solution is obtained having a temperature of about 40–50° C.

It should be noted how the sections 12, 14, 16 described up to now are of the known type, and therefore are not described any further.

A treatment section of the waste water 18 is also provided, as well of the type known in a urea production plant, which is in communication with the condensation section 16, through a connection line 42, to receive a possible part of the cold aqueous ammoniacal solution from it.

The treatment section of the waste water 18 is predisposed to recover carbon dioxide and ammonia from the cold aqueous ammoniacal solution, and is placed in fluid communication with the urea synthesis and recovery section 12 through a connection line 52.

The plant 10 also comprises a melamine synthesis section 20 from urea, which preferably comprises a melamine synthesis reactor adopting low pressure catalytic synthesis technology, as well of the known type.

The section 20 is connected to the urea treatment section 14 mentioned above through a connection line 21, for receiving at least part of the molten urea produced therein from it.

From the melamine synthesis section 20 the aforementioned off-gases, comprising amongst the various components also carbon dioxide and ammonia, are discarded.

The integrated plant 10 also comprises a treatment section of the off-gases 22 that comprises as main structures an absorption unit 70 predisposed for the condensation of the off-gases and a decomposition unit 72.

The absorption unit 70 is in fluid communication with the melamine synthesis section 20 through a connection line 54, to receive from such a section the off-gases discarded by it.

The absorption unit 70 and the decomposition unit 72 are in fluid communication through a connection line 76, equipped with a supply pump 78.

According to a first characteristic of the integrated plant 10 according to the present invention, the absorption unit 70 is also in fluid communication with the condensation section 16, to receive at least a fraction of the aforementioned cold aqueous ammoniacal solution from it to obtain the condensation of the off-gases.

The fluid communication is obtained through a connection line 56, which is directly joined with the aforementioned line 54 for inlet of the off-gases, upstream of the absorption unit 70, to allow a direct mixing of the off-gases with the cold aqueous ammoniacal solution.

At the outlet of the unit 70, a carbamate aqueous solution is thus obtained.

As highlighted in the detail of FIG. 3, the absorption unit 70 preferably comprises a condenser 84, an absorption column 86 placed in fluid communication through a connection line 88.

The condenser 84 preferably comprises a tube bundle apparatus placed in communication through a line 89 with a supply source of a cooling means, not illustrated in the figures, like for example cold water.

The absorption column 86 comprises a lower portion 86b in communication with the aforementioned connection line 88 and an upper portion 86a provided with a suitable packing.

In the lower portion 86b of the absorption column 86 possible gases not condensed in the condenser 84 are separated from the carbamate aqueous solution, which are further condensed through washing in the upper portion 86a. The uncondensed inert gases, on the other hand, are evacuated from the absorption column 86.

In particular, a connection line 90 for supplying washing water from a washing water reserve 94 to the upper zone 86a of the absorption column 86, and a connection line 96 between the top of the absorption column 86 and a possible section 98 of inert gases recovery, for the evacuation of the inert gases, are provided.

A recirculation line 100 is also provided to connect the intermediate zone of the absorption column 86 between the upper portion 86a and the lower portion 86b, and allow a recirculation of gases condensed by the column 86 in the condenser 84.

Downstream of the absorption unit 70 a preheating means or heater 110 is also preferably provided, arranged along the connection line 76 for increasing the temperature of the carbamate aqueous solution before the decomposition.

The aforementioned decomposition unit 72 preferably comprises, in this specific case, a decomposer or reboiler 102 and a desorption column 104 placed in fluid communication directly above the reboiler 102 and comprising a suitable packing.

As can clearly be seen from FIG. 3, the connection line 76 is in communication with the top zone of the desorption column 104, so as to introduce the carbamate solution from above after it has been heated.

The reboiler 102 comprises a tube bundle heat exchange apparatus that is in communication with a steam supply section 106. The reboiler 102 is also in communication with the aforementioned heater 110 through a connection line 112 to send the same condensed steam contained in the reboiler 102 as a heating means.

The decomposition of the carbamate solution takes place in the reboiler 102 obtaining on the one hand ammonia, carbon dioxide and steam, and on the other hand a residual aqueous ammoniacal solution.

In particular, ammonia, carbon dioxide and steam are evacuated from the top of the desorption column 104, and are supplied to the urea synthesis and recovery section 12 through a connection line 108, and preferably to the medium pressure recovery stage 28 of the section 12.

According to the invention, the decomposition section 72 is in fluid communication not only with the urea synthesis section 12, but also with the waste water treatment section 18 to supply the undistilled residual aqueous ammoniacal solution into it.

In particular, a connection line 114 is provided to supply the residual aqueous ammoniacal solution from the reboiler 102 to the waste water treatment section 18, where carbon dioxide and ammonia possibly remained in solution can be recovered.

The main advantage of the integrated plant 10 can be identified in the fact that the treatment section of the off-gases 22 is integrated, in direct fluid communication, both with the condensation section 16 and with the waste water treatment section 18, and this allows equipment predisposed for urea production to be used effectively and advantageously.

In particular, the fluid communication between the condensation section 16 and the absorption unit 70 allows the cold ammoniacal solution resulting from urea production to be exploited.

On the other hand, the fluid communication between the decomposition unit 72 and the waste water treatment section 18 relative to the urea production, allows a reduction in size of the equipment used for the desorption in the unit 72 to be obtained and does not require a total separation of the gases from the residual aqueous ammoniacal solution, precisely because they can be recovered without additional costs in the waste water treatment section 18 itself.

Another advantage of the present invention lies in the fact that thanks to the fluid communication between the condensation section 16, the waste water treatment section 18 and the treatment section of the off-gases 22, it is possible to vary the operating conditions of the apparatuses involved with a certain operative flexibility.

A further advantage of the present invention is due to the described particular specific structures of the absorption unit 70 and of the decomposition unit 72, which as well as being easy to construct, ensure an effective operative functionality of the two units.

Of course, a man skilled in the art can bring numerous modifications and variants to the integrated process for urea/melamine production and to the related plant, described above, in order to satisfy contingent and specific requirements, all of which are covered by the scope of protection of the invention, as defined by the following claims.

The invention claimed is:

1. Integrated process for urea/melamine production comprising the operating steps of:
 (a)—urea synthesis from ammonia and carbon dioxide, obtaining molten urea and a gaseous mixture comprising steam and ammonia;
 (b)—condensation of said gaseous mixture comprising steam and ammonia, obtaining a cold aqueous ammoniacal solution;
 (c)—melamine synthesis from urea with formation of off-gases, comprising ammonia and carbon dioxide;
 said process being characterized in that it comprises the further steps of:
 (d)—absorption of said off-gases in at least one fraction of the cold aqueous ammoniacal solution obtained in said step (b), with formation of a carbamate aqueous solution;
 (e)—decomposition of said carbamate aqueous solution, obtaining ammonia, carbon dioxide and steam, and a residual aqueous ammoniacal solution;
 (f)—recycling of the ammonia and of the carbon dioxide obtained in said step (e) for the urea synthesis;
 (g)—treatment of the residual aqueous ammoniacal solution obtained in said step (e) for the recovery from it of ammonia and carbon dioxide for the urea synthesis.

2. Process according to claim 1, wherein the residual aqueous ammoniacal solution obtained in said step (e) is added to part of the cold aqueous ammoniacal solution obtained in step (b), to constitute a single aqueous ammoniacal solution to be subjected to recovery treatment of urea synthesis gas in said step (g).

3. Process according to claim 1, wherein said cold aqueous ammoniacal solution is obtained through vacuum condensation (b).

4. Process according to claim 1, wherein the absorption of the off-gases (d) in the cold aqueous ammoniacal solution is carried out through a plurality of successive condensation stages, comprising at least one condensation stage by indirect heat exchange with a cooling means.

5. Process according to claim 4, wherein it comprises a further stage of separation of possible gases not absorbed and of recycling of said unabsorbed gases.

6. Process according to claim 1, wherein said carbamate aqueous solution, before being decomposed, is heated.

7. Integrated plant for urea and melamine production, of the type comprising:
 at least one synthesis and recovery section of urea in aqueous solution,
 at least one treatment section of the urea in solution to obtain molten urea and a gaseous mixture comprising steam and ammonia;

at least one condensation section of said gaseous mixture comprising steam and ammonia to obtain a cold aqueous ammoniacal solution;

at least one waste water treatment section predisposed to recover carbon dioxide and ammonia for the urea synthesis;

at least one melamine synthesis section;

at least one treatment section of the off-gases coming from the melamine synthesis section for their recycling to said urea synthesis and recovery section, and comprising at least one absorption unit placed in fluid communication with said melamine synthesis section and predisposed for the condensation of the off-gases with formation of a carbamate aqueous solution, and at least one decomposition unit placed in fluid communication with said absorption unit and predisposed to decompose said carbamate aqueous solution, obtaining carbon dioxide, ammonia and steam, and a residual aqueous ammoniacal solution; said plant being characterized in that said absorption unit is in fluid communication with said condensation section to receive at least a fraction of said cold aqueous ammoniacal solution from it for the condensation of the off-gases; and in that said waste water treatment section is in fluid communication with said decomposition unit to receive said residual aqueous ammoniacal solution from it.

8. Integrated plant according to claim 7, wherein said waste water treatment section is in communication with said condensation section to receive, from it, part of the cold aqueous ammoniacal solution not used for the absorption of the off-gases.

9. Integrated plant according to claim 7, wherein said urea synthesis and recovery section comprises a medium pressure recovery stage that is in fluid communication with said decomposition unit to receive carbon dioxide and ammonia from it.

10. Integrated plant according to claim 7, wherein said absorption unit comprises a condenser and an absorption column, arranged consecutively in fluid communication between said melamine synthesis section and said decomposition section.

11. Integrated plant according to claim 7, wherein said decomposition unit comprises a desorption column and a reboiler arranged consecutively in fluid communication downstream of said absorption unit.

12. Integrated plant according to claim 11, wherein said treatment section of the off-gases comprises a preheating means placed between said absorption unit and said decomposition unit to preheat the carbamate aqueous solution.

* * * * *